United States Patent
Wang et al.

(10) Patent No.: US 10,041,112 B2
(45) Date of Patent: Aug. 7, 2018

(54) MULTIPLEXED, CONTINUOUS-FLOW, DROPLET-BASED PLATFORM FOR HIGH-THROUGHPUT GENETIC DETECTION

(71) Applicants: The Johns Hopkins University, Baltimore, MD (US); Pioneer Hi-Bred International, Inc., Johnston, IA (US)

(72) Inventors: Tza-Huei J. Wang, Baltimore, MD (US); Kuangwen Hsieh, Germantown, MD (US); Helena C. Zec, Baltimore, MD (US); Lingshu Liu, Baltimore, MD (US); Aniruddha M. Kaushik, Baltimore, MD (US); Yue Yun, Johnston, IA (US)

(73) Assignees: The Johns Hopkins University, Baltimore, MD (US); Pioneer Hi-Bred International, Inc., Johnston, IA (US)

( * ) Notice: Subject to any disclaimer, the term of this patent is extended or adjusted under 35 U.S.C. 154(b) by 170 days.

(21) Appl. No.: 15/097,904

(22) Filed: Apr. 13, 2016

(65) Prior Publication Data
US 2016/0298173 A1     Oct. 13, 2016

Related U.S. Application Data

(60) Provisional application No. 62/146,774, filed on Apr. 13, 2015.

(51) Int. Cl.
*B01L 3/00* (2006.01)
*B01L 7/00* (2006.01)
(Continued)

(52) U.S. Cl.
CPC ........ *C12Q 1/686* (2013.01); *B01L 3/502784* (2013.01); *B01L 7/525* (2013.01);
(Continued)

(58) Field of Classification Search
CPC ........ C12Q 2563/107; C12Q 2565/629; C12Q 1/686; C12Q 1/6869; C12Q 2531/113;
(Continued)

(56) References Cited

U.S. PATENT DOCUMENTS

| 2005/0048581 A1* | 3/2005 | Chiu | ........... B01L 3/502761 435/7.1 |
| 2008/0280331 A1* | 11/2008 | Davies | ........... B01L 7/525 435/91.2 |

(Continued)

OTHER PUBLICATIONS

Abate et al., *Proc. Natl. Acad. Sci. U. S. A.*, 2010, 107, 19163-19166.
(Continued)

*Primary Examiner* — Jennifer Wecker
(74) *Attorney, Agent, or Firm* — Venable, LLP; Henry J. Daley; Miguel A. Lopez

(57) ABSTRACT

The present application relates to a continuous droplet flow microfluidic system, including a microfluidic chip including an optical detection section; a stage assembly including a microfluidic chip holder configured to receive the microfluidic chip and a plurality of heating elements arranged to heat a plurality of separate sections of the microfluidic chip to a corresponding plurality of different temperatures; and an optical detection system arranged to detect fluorescent light emitted from said optical detection section of the microfluidic chip.

18 Claims, 7 Drawing Sheets

(51) Int. Cl.
*B01L 9/00* (2006.01)
*C12Q 1/68* (2018.01)
*C12Q 1/686* (2018.01)
*C12Q 1/6869* (2018.01)
*B01L 3/02* (2006.01)

(52) U.S. Cl.
CPC .......... *C12Q 1/6869* (2013.01); *B01L 3/0241* (2013.01); *B01L 2200/0673* (2013.01); *B01L 2300/0654* (2013.01); *B01L 2300/0816* (2013.01); *B01L 2300/0867* (2013.01); *B01L 2300/0877* (2013.01); *B01L 2300/0883* (2013.01); *B01L 2300/1822* (2013.01)

(58) Field of Classification Search
CPC ....... C12Q 2535/122; B01L 2200/0673; B01L 2300/0654; B01L 2300/0816; B01L 2300/0867; B01L 2300/0877; B01L 2300/0883; B01L 2300/1822; B01L 3/0241; B01L 3/502784; B01L 7/525
See application file for complete search history.

(56) References Cited

U.S. PATENT DOCUMENTS

| | | | | |
|---|---|---|---|---|
| 2010/0173394 | A1* | 7/2010 | Colston, Jr. ........... | B01F 3/0807 435/287.2 |
| 2013/0165346 | A1* | 6/2013 | Wang ...................... | G01N 1/28 506/12 |
| 2013/0252262 | A1* | 9/2013 | Srinivasan ............. | G01N 27/72 435/7.72 |

OTHER PUBLICATIONS

Abramoff et al., Image Processing with ImageJ *Biophotonics International* 2004, 11, 36-42.
Adamson et al., Production of arrays of chemically distinct nanolitre plugs via repeated splitting in microfluidic devices *Lab. Chip* 2006, 6, 1178-1186.
Baret et al., *Lab. Chip*, 2009, 9, 1850-1858.
Beer, B. J. Hindson, E. K. Wheeler, S. B. Hall, K. A. Rose, I. M. Kennedy and B. W. Colston, *Anal. Chem.*, 2007, 79, 8471-8475.
Boedicker et al., *Lab. Chip*, 2008, 8, 1265-1272.
Brouzes et al., Droplet microfluidic technology for single-cell high-throughput screening *Proc. Natl. Acad. Sci. U. S. A.* 2009, 106, 14195-14200.
Chen et al., Microfluidic cartridges preloaded with nanoliter plugs of reagents: an alternative to 96-well plates for screening *Curr. Opin. Chem. Biol.* 2006, 10, 226-231.
Clausell-Tormos et al., *Chem. Biol.*, 2008, 15, 427-437.
Guo et al., *Lab. Chip*, 2012.
Guo et al., Appl. Phys. Lett., 2010, 97, 233701-3.
Gupta et al., Heredity (Edinb), 2008, 101, 5-18.
Huebner et al., Chem. Commun. (Camb), 2007, (12), 1218-1220 et al.
Huebner et al., Lab. Chip, 2008, 8, 1244-1254.
Kim et al. "Ultra-low voltage MEMS switch using a folded hinge structure," Micro and Nano Systems Letters, 2, 2 (2014).
Kiss et al., Anal. Chem., 2008, 80, 8975-8981.
Kumaresan, et al., Anal. Chem., 2008, 80, 3522-3529.
Li et al., Nanoliter microfluidic hybrid method for simultaneous screening and optimization validated with crystallization of membrane proteins Proc. Natl. Acad. Sci. U. S. A. 2006, 103, 19243-19248.
Linder et al., Reagent-loaded cartridges for valveless and automated fluid delivery in microfluidic devices Anal. Chem. 2005, 77, 64-71.
Mayr et al., Novel trends in high-throughput screening Curr. Opin. Pharmacol. 2009, 9, 580-588.
Melin et al., Annu. Rev. Biophys. Biomol. Struct., 2007, 36, 213-231.
Pompano et al., Annu. Rev. Anal. Chem. (Palo Alto Calif), 2011, 4, 59-81.
Puleo et al., Lab. Chip, 2009, 9, 1065-1072.
Puleo et al., Lab. Chip, 2008, 8, 822-825.
Qu et al. "Droplet electroporation in microfluidics for efficient cell transformation with or without cell wall removal," Lab on a Chip, 12, 4483 (2012).
Ragoussis, Annu. Rev. Genomics Hum. Genet., 2009, 10, 117-133.
Rane et al., Counting single molecules in sub-nanolitre droplets Lab. Chip 2010, 10, 161-164.
Shi et al., *Lab. Chip*, 2010, 10, 2855-2863.
Shi et al., *Lab. Chip*, 2008, 8, 1432-1435.
Sobrino et al., *Forensic Sci. Int*, 2005, 154, 181-194.
Song et al., Angew. Chem. Int. Ed Engl., 2006, 45, 7336-7356.
Teh et al., Droplet microfluidics Lab. Chip 2008, 8, 198-220.
Tewhey et al., Nat. Biotechnol., 2009, 27, 1025-1031.
Theberge et al., Lab. Chip, 2012, 12, 1320-1326.
Unger et al., Science, 2000, 288, 113-116.
Veldhuisen et al., Vox Sang., 2009, 97, 198-206.
Wang et al., ACS Nano, 2010, 4, 6235-6243.
Yeon et al. "Microfluidic cell culture systems for cellular analysis," BioChip Journal, 1, 17 (2007).
Zeng et al., Lab. Chip, 2009, 9, 1340-1343 (DOI:10.1039/b821803j).
Zhang et al., Microfluidic DNA amplification—a review Anal. Chim. Acta 2009, 638, 115-125.
Zheng et al., A microfluidic approach for screening submicroliter volumes against multiple reagents by using preformed arrays of nanoliter plugs in a three-phase liquid/liquid/gas flow Angew. Chem. Int. Ed Engl. 2005, 44, 2520-2523.
Zhong et al., Multiplex digital PCR: breaking the one target per color barrier of quantitative PCR Lab. Chip 2011, 11, 2167-2174.

* cited by examiner

MULTIPLEXED, CONTINUOUS-FLOW, DROPLET-BASED PLATFORM FOR HIGH-THROUGHPUT GENETIC DETECTION

CROSS-REFERENCE OF RELATED APPLICATION

This application claims priority to U.S. Provisional Application No. 62/146,774, filed on Apr. 13, 2015; the entire contents of all of which are hereby incorporated by reference.

This invention was made with Government support under R21 CA120742, awarded by the Department of Health and Human Services, The National Institutes of Health (NIH). The U.S. Government has certain rights in this invention.

BACKGROUND

1. Field of Invention

The field of the currently claimed embodiments of this invention relates to microfluidic systems, and more particularly to a multiplexed, continuous-flow, droplet-based platform for high-throughput genetic detection.

2. Discussion of Related Art

High throughput sample processing is a critical requirement for a large number of industries. Some examples include the agricultural, pharmaceutical and biotechnological industries[1]. As a result, there is a constant drive for innovation in sample processing techniques to support these industries. One major breakthrough in this domain has been the application of various robotic sample handling techniques to improve the speed of sample processing as well as to reduce the volume of reagents used per reaction. Although the robotic systems have become incredibly fast at sample processing operations, they are typically limited to operating with standard multi-well (96, 384 and 1536 well) plates. As a result, the typical sample volume consumption is on the order of microliters per reaction for such systems[1]. Recent advances in the microfluidic domain show promise in overcoming this limitation of the robotic systems. Droplet-based microfluidic systems have been shown to be capable of performing biomolecular screening with sample volumes as low as picoliters[2-6]. However, introducing a large number of samples on a miniature microfluidic device is difficult since it is impractical to have hundreds to thousands of sample inlets to a single microfluidic device. Furthermore, the tubing used for supplying the samples to such a microfluidic device would already consume orders of magnitude more sample than is required for the actual analysis on the microfluidic device. So, there is a need for an efficient way to transport a large number of samples to a microfluidic device. Ideally such a sample transport system would be flexible enough to supply variable number of samples to a microfluidic device without any modifications in the transport system or the device.

The 'plug-in cartridge' technique developed by the Whitesides group[7] provides an elegant solution to the problem of introducing a large number of reagents on a microfluidic device through a single inlet. Under this approach, a series of sample plugs are loaded into a capillary, with air bubbles present between sample plugs acting as spacers. This capillary is connected to a microfluidic device, for serial delivery of these sample plugs. However, in this approach, the sample plugs are constantly in contact with the capillary inner surface, leading to the problem of cross contamination between plugs[7]. Another modification of this approach developed by the Ismagilov group[8] utilizes an immiscible carrier fluid instead of an air bubble to act as a spacer between sample plugs. The carrier fluid in this approach preferentially wets the inner surface of the capillary, thus preventing direct contact between sample plugs and the capillary surface. As a result, the problem of cross contamination between sample plugs is eliminated. The carrier fluids typically used for generating these sample plug arrays are fluorinated oils, which also reduce the problem of reagents leaking from sample plugs into the carrier fluid due to their low solubility for most reagents[8].

Although this approach is promising, the current techniques used under this approach for generating the 'sample plug cartridges' have some issues which need to be resolved. The common technique of using a syringe pump for aspirating sample plugs from a sample well[9-11] in a multi-well plate can be extremely slow. Another technique of using vacuum for aspirating a sample plug can be much faster[7]. However, this technique can only provide a maximum driving pressure of 1 atm (~15 psi). As a result, the driving force may not be sufficient to load large numbers of sample plugs into a capillary due to the increasing fluidic resistance of the capillary with the introduction of sample plugs. Furthermore, both of these techniques require the free end of the capillary to be attached to either a syringe or a vacuum source, thus excluding the possibility of operating this sample loading system in sync with the operations on a downstream microfluidic device. This can be a major setback to throughput as the possibility of conducting assays in continuous flow manner on microfluidic devices, as has been demonstrated earlier[12], is precluded.

For example, maintaining global crop production has become increasingly important amidst a growing global population, and together with water scarcity, pollution, decreasing arable land, emergence of new pests, and possible climate change pose significant challenges. Toward this end, genetic marker assisted selection (MAS), wherein the plant breeding process relies on known DNA/RNA variations associated with traits of interest (e.g., productivity and disease resistance), has enormous potential to improve the efficiency and precision of conventional plant breeding. Traditional techniques for performing MAS at the scale required for agricultural applications, which requires detecting a large number of markers for a large number of plant samples, involve robotic sample handlers, require large amounts of precious samples (>microliter), and are extremely expensive and relatively slow. Droplet microfluidic devices are capable of high-throughput screening using a compact and inexpensive setup compared to robotic sample handlers, and more importantly, reducing sample volume consumption to the nanoliter regime per reaction, some three orders of magnitude reduction in sample consumption. However, existing droplet microfluidic devices have yet to achieve highly multiplexed genetic detection assays in a continuous-flow and high-throughput manner, thus rendering them impractical for the intended applications. Our platform according to some embodiments of the current invention can solve this critical problem and open the door for droplet microfluidic devices to a host of genetic detection assays for high-throughput MAS.

Therefore, there remains a need for improved multiplexed, continuous-flow, droplet-based platforms for high-throughput genetic detection.

REFERENCES FOR BACKGROUND SECTION (1) Mayr, L. M.; Bojanic, D. Novel trends in high-throughput screening *Curr. Opin. Pharmacol.* 2009, 9, 580-588.

(2) Teh, S. Y.; Lin, R.; Hung, L. H.; Lee, A. P. Droplet microfluidics *Lab. Chip* 2008, 8, 198-220.
(3) Rane, T. D.; Puleo, C. M.; Liu, K. J.; Zhang, Y.; Lee, A. P.; Wang, T. H. Counting single molecules in sub-nanolitre droplets *Lab. Chip* 2010, 10, 161-164.
(4) Brouzes, E.; Medkova, M.; Savenelli, N.; Marran, D.; Twardowski, M.; Hutchison, J. B.; Rothberg, J. M.; Link, D. R.; Perrimon, N.; Samuels, M. L. Droplet microfluidic technology for single-cell high-throughput screening *Proc. Natl. Acad. Sci. U.S.A.* 2009, 106, 14195-14200.
(5) Kiss, M. M.; Ortoleva-Donnelly, L.; Beer, N. R.; Warner, J.; Bailey, C. G.; Colston, B. W.; Rothberg, J. M.; Link, D. R.; Leamon, J. H. High-throughput quantitative polymerase chain reaction in picoliter droplets *Anal. Chem.* 2008, 80, 8975-8981.
(6) Zhong, Q.; Bhattacharya, S.; Kotsopoulos, S.; Olson, J.; Taly, V.; Griffiths, A. D.; Link, D. R.; Larson, J. W. Multiplex digital PCR: breaking the one target per color barrier of quantitative PCR *Lab. Chip* 2011, 11, 2167-2174.
(7) Linder, V.; Sia, S. K.; Whitesides, G. M. Reagent-loaded cartridges for valveless and automated fluid delivery in microfluidic devices *Anal. Chem.* 2005, 77, 64-71.
(8) Chen, D. L.; Ismagilov, R. F. Microfluidic cartridges preloaded with nanoliter plugs of reagents: an alternative to 96-well plates for screening *Curr. Opin. Chem. Biol.* 2006, 10, 226-231.
(9) Zheng, B.; Ismagilov, R. F. A microfluidic approach for screening submicroliter volumes against multiple reagents by using preformed arrays of nanoliter plugs in a three-phase liquid/liquid/gas flow *Angew. Chem. Int. Ed Engl.* 2005, 44, 2520-2523.
(10) Adamson, D. N.; Mustafi, D.; Zhang, J. X.; Zheng, B.; Ismagilov, R. F. Production of arrays of chemically distinct nanolitre plugs via repeated splitting in microfluidic devices *Lab. Chip* 2006, 6, 1178-1186.
(11) Li, L.; Mustafi, D.; Fu, Q.; Tereshko, V.; Chen, D. L.; Tice, J. D.; Ismagilov, R. F. Nanoliter microfluidic hybrid method for simultaneous screening and optimization validated with crystallization of membrane proteins *Proc. Natl. Acad. Sci. U.S.A.* 2006, 103, 19243-19248.
(12) Zhang, Y.; Ozdemir, P. Microfluidic DNA amplification—a review *Anal. Chim. Acta* 2009, 638, 115-125.
(13) Abramoff, M. D.; Magalhaes, P. J.; Ram, S. J. Image Processing with ImageJ *Biophotonics International* 2004, 11, 36-42.

SUMMARY

Some embodiments of the instant invention include a continuous droplet flow microfluidic system, comprising: a microfluidic chip comprising an optical detection section; a stage assembly comprising a microfluidic chip holder configured to receive said microfluidic chip and a plurality of heating elements arranged to heat a plurality of separate sections of said microfluidic chip to a corresponding plurality of different temperatures; and an optical detection system arranged to detect fluorescent light emitted from said optical detection section of said microfluidic chip, wherein said microfluidic chip includes: a substrate; a channel control layer attached to said substrate; and a fluid flow layer attached to said channel control layer on an opposite side of said control layer from said substrate such that said fluid flow layer and said channel control layer define fluid channels within said fluid flow layer, said channel control layer and said fluid flow layer being formed from materials that do not require surface treatment for fluid flow through said fluid channels, wherein said channel control layer and said fluid flow layer define a main channel extending from a droplet generating section, extending through a reagent injection section, passing through a plurality of incubation sections, each incubation section having a separately selectable temperature, and passing through said optical detection section, wherein said main channel increases in width and height between said reagent injection section and said plurality of incubation sections, and wherein said optical detection section of said main channel has at least one of a decreased width or decreased height relative to said plurality of incubation sections to stretch droplets for detection.

Some embodiments of the instant invention include a microfluidic chip, comprising: a substrate; a channel control layer attached to said substrate; and a fluid flow layer attached to said channel control layer on an opposite side of said control layer from said substrate such that said fluid flow layer and said channel control layer define fluid channels within said fluid flow layer, said channel control layer and said fluid flow layer being formed from materials that do not require surface treatment for fluid flow through said fluid channels, wherein said channel control layer and said fluid flow layer define a main channel extending from a droplet generating section, extending through a reagent injection section, passing through a plurality of incubation sections, each incubation section having a separately selectable temperature, and passing through an optical detection section, wherein said main channel increases in width and height between said reagent injection section and said plurality of incubation sections, and wherein said optical detection section of said main channel has at least one of a decreased width or decreased height relative to said plurality of incubation sections to stretch droplets for detection.

BRIEF DESCRIPTION OF THE DRAWINGS

Further objectives and advantages will become apparent from a consideration of the description, drawings, and examples.

DETAILED DESCRIPTION

Figure 1A:
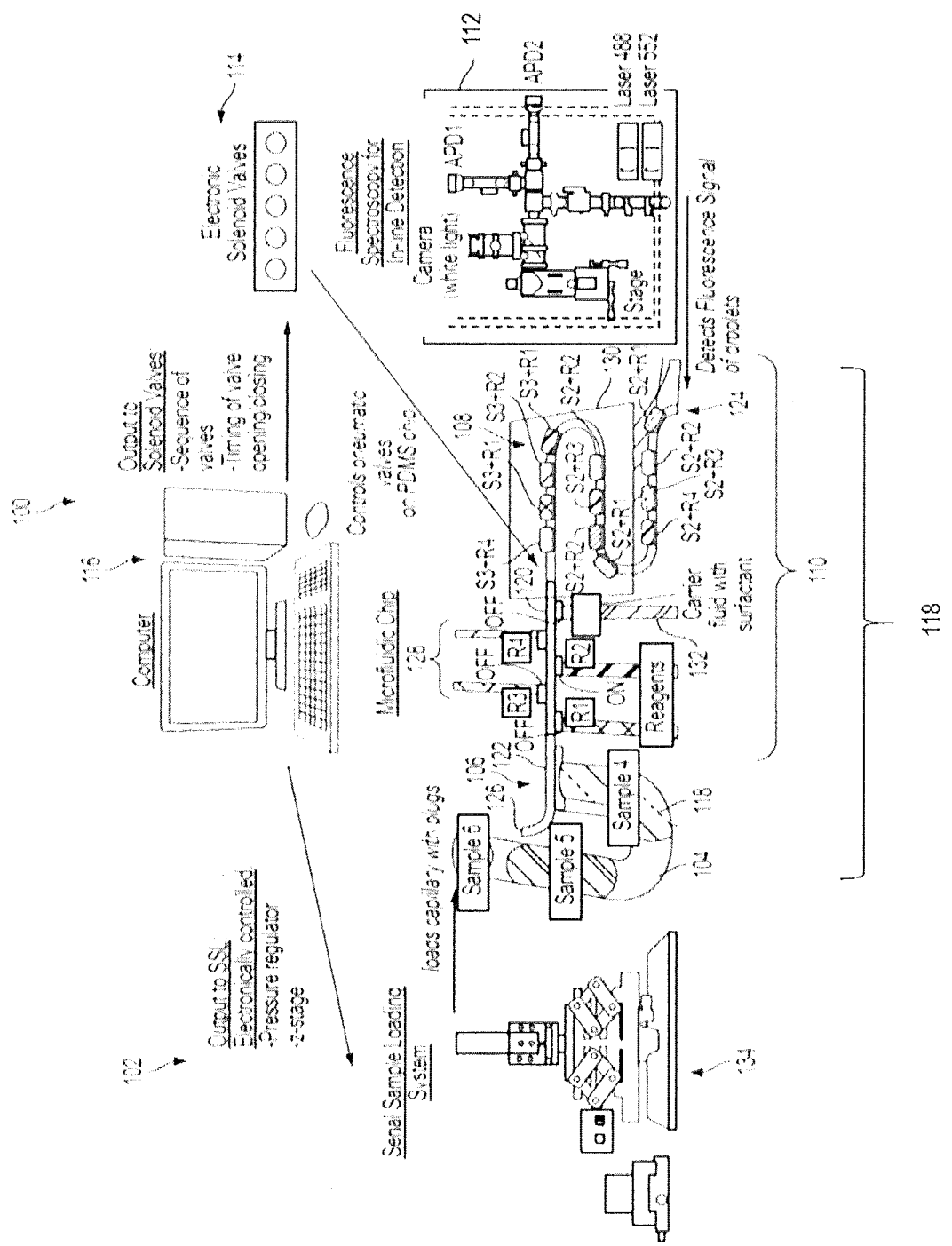
FIG. 1A is a schematic illustration of a continuous throughput microfluidic system according to an embodiment of the current invention.

Some embodiments of the current invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention. All references cited anywhere in this specification, including the Background and Detailed Description sections, are incorporated by reference as if each had been individually incorporated. In particular, the previously filed U.S. patent application Ser. No. 13/708,510 (Pub. No. US 2013/0165346 A1) by many of the current inventors is hereby incorporated by reference.

The aforementioned droplet platforms do not address the needs of numerous applications which require high degrees of multiplexing as well as high-throughput analysis of multiple samples. Some examples include, but are not limited to, genetic fingerprinting for forensics[14], single nucleotide polymorphism (SNP) analysis for crop improvement and domestication[15], genotyping required for identification of genes associated with common diseases[16] and generation of a blood donor genotype database for better matching between recipient and donor to prevent adverse transfusion reactions[17]. All of these applications require multiplexed screening of a single sample with a panel of reagents (or markers) and rapid screening of a large number of samples to generate the required databases.

In recent years, there have been attempts to expand the capacity of droplet platforms for the analysis of a biological or chemical sample with multiple reagents. One of the well-tested platforms has been the droplet platform developed by RainDance Technologies, for massively parallel PCR enrichment for DNA sequencing[18]. This platform involves a multistep approach with generation of a large library of PCR reagent droplets by a microchip, followed by merging of these reagent droplets with sample droplets generated from a DNA sample on a second device. These sample-reagent hybrid droplets are then collected in standard PCR tubes for thermocycling, followed by fluorescence detection and sequencing. In this platform, the content of each individual droplet is unknown and is decoded only by offline nucleic acid sequencing. Therefore, it cannot be applied to other applications that require real-time detection[4]. A solution to this problem is to associate a unique optical code with each reagent prior to mixing with the sample[19]. However, an optical-coding scheme based on fluorescence intensity is practically limited to a small number of 'codes' due to the small allowable number of fluorophores without spectral crosstalk and the limited dynamic range of the optical detection setup being used[4]. Furthermore, the electrocoalescence technique used in such platforms for droplet merging is susceptible to errors of no fusion caused by an excess of droplets of a reagent or unintended fusion of more than two droplets due to highly stringent synchronization requirements[20]. A recent article demonstrated a pico-injector which can overcome this problem and be used to add controlled volumes of multiple reagents to sample droplets using electromicrofluidics[21]. However, similar to droplet platforms discussed earlier, the content of each individual droplet is unknown unless a barcode is included in each individual droplet.

Alternatively, a series of articles adopted a cartridge technique for increasing the throughput of the droplet platform[22]. This technique involves generation of an array of reagent plugs in a capillary (cartridge), which are sequentially introduced to a simple microfluidic device for merging with a single substrate. The reagent plugs can be further digitized into smaller droplets prior to merging with the sample. As the length of the capillary can be very long, the number of reagents to screen against the sample is virtually limitless. This technique has been applied to many applications including protein crystallization[22] and study of bacterial susceptibility to antibiotics[23]. Although the aforementioned droplet and cartridge platforms are capable of high throughput and multiplexed analysis, they are still limited to screening of a single sample at a time.

Recently, a microfluidic platform was proposed for combinatorial chemical synthesis in picolitre droplets, where droplets of one library of reagents were fused at random with droplets containing a different set of reagents[20]. This platform has the potential of generating a large set of possible combinations of different reagents. However, as afore-discussed, the unknown identity of the compounds within individual droplets precludes its use for many screening applications that require real-time detection.

Some embodiments of the current invention provide a droplet platform capable of on-demand generation of nano-litre droplets of combinational mixtures of samples and reagents needed for biochemical screening applications that require multiplexing and high-throughput capability. On-demand droplet generation and manipulation using pneumatic valves has been demonstrated by other groups in the past[24-26]. However, these platforms have focused on generating multiple reagent combinations using fixed number of inputs to the device, severely limiting the number of possible sample-reagent combinations being generated on the device. The droplet platform according to some embodiments of the current invention uses a linear array of sample plugs as an input to the device, removing the limitation imposed by the number of inputs to the device. Initially, a preformed linear array of sample plugs separated by a carrier fluid is flowed from the cartridge into the microfluidic device, wherein each plug is digitized by a pneumatic valve into smaller sample daughter droplets. The volume of the resulting daughter droplet can be precisely controlled by varying the valve opening time and the back pressure on the cartridge containing sample plugs. The daughter droplets are then directly injected with reagents in a synchronization-free manner. The microfluidic design features a robust fusion module which exploits local channel geometry for synchronization-free injection of reagents into each sample daughter droplet. After reagent injection into a sample droplet, a microfluidic device according to some embodiments of the current invention introduces additional carrier fluid containing surfactant to the channel containing the sample-reagent hybrid droplet array to prevent unwanted merging of these droplets on the device. In an embodiment of the microfluidic device, droplets are indexed by their layout in a 1D array, enabling the identification of the contents of each droplet by spatial indexing. Spatial indexing as a means for identification of droplet content can obviate the need for a limiting optical barcoding scheme.

Some embodiments of the instant invention include a continuous droplet flow microfluidic system, comprising: a microfluidic chip comprising an optical detection section; a stage assembly comprising a microfluidic chip holder configured to receive said microfluidic chip and a plurality of heating elements arranged to heat a plurality of separate sections of said microfluidic chip to a corresponding plurality of different temperatures; and an optical detection system arranged to detect fluorescent light emitted from said optical detection section of said microfluidic chip, wherein said microfluidic chip includes: a substrate; a channel control layer attached to said substrate; and a fluid flow layer attached to said channel control layer on an opposite side of said control layer from said substrate such that said fluid flow layer and said channel control layer define fluid channels within said fluid flow layer, said channel control layer and said fluid flow layer being formed from materials that do not require surface treatment for fluid flow through said fluid channels, wherein said channel control layer and said fluid flow layer define a main channel extending from a droplet generating section, extending through a reagent injection section, passing through a plurality of incubation sections, each incubation section having a separately selectable temperature, and passing through said optical detection section, wherein said main channel increases in width and height between said reagent injection section and said plurality of incubation sections, and wherein said optical detection section of said main channel has at least one of a decreased width or decreased height relative to said plurality of incubation sections to stretch droplets for detection.

Some embodiments of the invention include a droplet flow microfluidic system, wherein a droplet generating section is configured to receive a capillary comprising a plurality of sample plugs separated by an immiscible carrier fluid and to generate a plurality of droplets from each of said plurality of sample plugs.

Some embodiments of the invention include a droplet flow microfluidic system, wherein a droplet generating section is configured to receive a droplet generator.

Some embodiments of the invention include a droplet flow microfluidic system, further comprising an input system in fluid communication with a droplet generator, wherein said input system is configured to provide a sequential stream of sample plugs, and wherein said droplet generator is configured to receive the sequential stream of sample plugs.

Some embodiments of the invention include a droplet flow microfluidic system, further comprising a droplet treatment system arranged in fluid connection with a droplet generator.

Some embodiments of the invention include a droplet flow microfluidic system, wherein a droplet generator is configured to provide a stream of treated droplets in a sequential order.

Some embodiments of the invention include a droplet flow microfluidic system, wherein a droplet generator further comprises a valve assembly.

Some embodiments of the invention include a droplet flow microfluidic system, wherein a plurality of generated droplets are between 0.1 nL and 200 nL.

Some embodiments of the invention include a droplet flow microfluidic system, wherein a plurality of generated droplets are between 0.5 nL and 100 nL.

Some embodiments of the invention include a droplet flow microfluidic system, wherein a reagent injection section is configured to allow selected injection of at least one of a plurality of reagents into selected droplets as the droplets pass through said reagent injection section.

Some embodiments of the invention include a droplet flow microfluidic system, wherein a main channel has a serpentine path in each incubation section of said plurality of incubation sections.

Some embodiments of the invention include a droplet flow microfluidic system, including an optical detection system that is a multi-color confocal fluorescence spectroscopic system.

Some embodiments of the instant invention include a microfluidic chip, comprising: a substrate; a channel control layer attached to said substrate; and a fluid flow layer attached to said channel control layer on an opposite side of said control layer from said substrate such that said fluid flow layer and said channel control layer define fluid channels within said fluid flow layer, said channel control layer and said fluid flow layer being formed from materials that do not require surface treatment for fluid flow through said fluid channels, wherein said channel control layer and said fluid flow layer define a main channel extending from a droplet generating section, extending through a reagent injection section, passing through a plurality of incubation sections, each incubation section having a separately selectable temperature, and passing through an optical detection section, wherein said main channel increases in width and height between said reagent injection section and said plurality of incubation sections, and wherein said optical detection section of said main channel has at least one of a decreased width or decreased height relative to said plurality of incubation sections to stretch droplets for detection.

Some embodiments of the instant invention include a microfluidic chip, including a droplet generating section that is configured to receive a capillary comprising a plurality of sample plugs separated by an immiscible carrier fluid and to generate a plurality of droplets from each of said plurality of sample plugs.

Some embodiments of the instant invention include a microfluidic chip, wherein a generated plurality of droplets are between 0.1 nL and 200 nL.

Some embodiments of the instant invention include a microfluidic chip, wherein a generated plurality of droplets are between 0.5 nL and 100 nL.

Some embodiments of the instant invention include a microfluidic chip, wherein a reagent injection section is configured to allow selected injection of at least one of a plurality of reagents into selected droplets as the droplets pass through said reagent injection section.

Overall Platform

This platform has 1) a droplet microfluidic device and 2) a multi-temperature and optical detection apparatus. Together, the platform allows the first demonstration of highly multiplexed genetic detection assays to be performed within droplet microfluidic devices in a continuous-flow and high-throughput manner.

Microfluidic Device

Uniform Surface within Microfluidic Channel: A microfluidic device (also referred to as a microfluidic chip) according to an embodiment of the current invention uses an updated silicone polymer material multi-layer technique that places the fluidic layer above the valve control layer. Such design creates a uniform, all-silicone polymer material surface within the microchannels, as opposed to the hybrid, glass-silicone polymer material surface commonly employed in previous designs. In some embodiments, the silicone polymer material is polydimethylsiloxane (PDMS).

No Surface Treatment Required: The all-silicone polymer material surface within the microchannel obviates surface treatment with Aquapel™, a chemical that is universally used in droplet microfluidic devices that have caused significant degradation of fluorescence signal.

Use of Channel Geometry for Robust Droplet Formation, Transport, and Detection: After injection reagents into the sample droplet, the channel widens to allow any small droplets that had broken during the injection process to recombine with the original droplet. Prior to reaching the incubation region, both the channel width and height increased, which slowed the droplet movement to ensure appropriate incubation time. Finally, the channel narrows prior to the detection zone, which stretches the length of the droplet and allows the droplet to be detected for a longer period of time, thus enhancing the robustness of droplet detection.

Multi-Temperature and Optical Detection Apparatus

This apparatus according to an embodiment of the current invention harbors three independent temperature zones and an optical detection window. Three temperature-controlled peltier heaters are thermally glued to the three temperature zones of the plate to deliver the required temperatures for PCR. The detection window allows fluorescence detection of each droplet in a sequential manner via a custom-built, multi-color confocal fluorescence spectroscopic (CFS) instrument. The multi-temperature setup offers flexibility of any temperature conditions required to perform different types of assays such as PCR (requires two or three temperatures) or Invader (require one temperature).

A embodiment of this platform uses a semi-automatic sample loading system, where the operator uses custom software to control the injection of samples from a multiwell plate into a tubing (or a capillary) connected to the microfluidic device. Switching between sample wells requires additional control using the software. According to some embodiments of the platform according to the current invention, this can be full automated.

In some embodiments, genetic marker probes can be introduced in the continuous phase format. However, to improve multiplexing capability and maintain compactness, alternative embodiments may introduce probes also using the sample loading system in the form of a linear sample array that is analogous to the current format of sample introduction.

An embodiment of the microfluidic device uses a single main channel for sample/probe mixing and incubation, and uses a single detector to detect the droplets at a single, fixed position. In the interest of performing multiple experiments under the same conditions (to improve robustness) and increasing the assay throughput, the channel architecture can be modified according to some embodiments of the current invention to split droplets into multiple numbers of daughter droplets that would then be incubated and detected in independent channels. Likewise, the detection platform can be modified by implementing a linear CCD device so that droplets in different channels can be detected in parallel.

Although the intended application of this platform is genetic amplification and detection assays such as Polymerase Chain Reaction (PCR) and the Invader assay, the platform can be used for other applications that require multiple components and different temperature requirements.

Systems and methods for screening a library of samples are described in U.S. Patent Application Publication No. US 2013/0165346 A1, published on Jun. 27, 2013, the entire contents of which are hereby incorporated by reference.

FIG. 1A is a schematic illustration of a continuous throughput microfluidic according to an embodiment of the current invention. The continuous throughput microfluidic system 100 includes an input system 102 configured to provide a sequential stream of sample plugs 104, a droplet generator 106 arranged in fluid connection with the input system 102 to receive the sequential stream of sample plugs 104. The term "plug" is used here to indicate that it is a larger volume than the droplets such that one plug can be used to generate a plurality of droplets. The general concepts of the current invention are not limited by a particular number of droplets produced from each plug. The droplet generator 106 is also configured to provide an output stream of droplets (not shown in FIG. 1A). The continuous throughput microfluidic system 100 also includes a droplet treatment system 110 arranged in fluid connection with the droplet generator 106 to receive the output stream of droplets in a sequential order. The droplet generator 106 is also configured to provide a stream of treated droplets 108 in the sequential order, a few of which are illustrated in FIG. 1A. The continuous throughput microfluidic system 100 also includes a detection system 112 arranged to obtain detection signals from the treated droplets in the sequential order. The continuous throughput microfluidic system 100 further includes a control system 114 configured to communicate with the input system 102, the droplet generator 106, and the droplet treatment system 110. The continuous throughput microfluidic system 100 also includes a data processing and storage system 116 configured to communicate with the control system 114 and the detection system 112.

The data processing and storage system 116 can be, but is not limited to, a programming computer, for example. The computer can be a localized computer, such as, but not limited to, a lap top computer, a desk top computer, or a workstation. However, the computer can also be a distributed system, such as a networked system of computers. The control system 114 can similarly have programming components implemented on the same of different computer as data processing and storage system 116. The data processing and storage system 116 and/or control system 114 can also include hard wired electronic components in addition to, or instead of software implemented functions.

The control system 114 is configured to control the input system 102 in conjunction with the droplet generator 106 and to provide information to the data processing and storage system 116 that identifies each droplet of the output stream of droplets with a corresponding sample plug of said sequential stream of sample plugs 104. The control system 114 further controls the droplet treatment system 110 and provides information to the data processing and storage system 116 that identifies a treatment applied to each droplet of the output stream of droplets. The data processing and storage system 116 receives the detection signals and calculates a property of each treated droplet and identifies a corresponding plug and treatment for each treated droplet based on the sequential order.

In some embodiments continuous throughput microfluidic system 100 can include a microfluidic chip 118 that defines a microfluidic channel 120 that includes an input end 122 configured to be fluidly connected to the input system 102. As illustrated in the example of FIG. 1A, microfluidic channel 120 can have a first segment that is integrated with the droplet generator 106, a second segment that is integrated with the droplet treatment system 110, and a third segment that provides a measurement region 124 for the detection system 112. The term "microfluidic" channel means that the channel has cross-sectional dimensions that are less than one millimeter. For example, for an approximately circular cross-sectional channel, the channel diameter is less than one millimeter. For a square or rectangular cross-sectional channel, the channel height and width are both less than one millimeter. In some embodiments. The channel cross-sectional dimensions can be tens of microns, a few microns, or even less than one micron.

The microfluidic chip 118 can have multiple sections for performing multiple functions, as is illustrated in FIG. 1A and illustrated in more detail below. Other embodiments of the current invention could combine two or more microfluidic chips for performing the desired functions without departing from the broad concepts of the current invention.

The microfluidic chip 118 in the embodiment of FIG. 1A further defines a valve assembly (not shown) as a component of the droplet generator 106 that is selectively controllable by the control system 114. The droplet generator 106 also includes a fluid channel 126 for receiving carrier fluid to be input into the microfluidic channel 120 between adjacent droplets. The treatment system 110 can include a reagent adding section 128 and at least one of a reaction section or an incubation section 130, for example. The treatment system 110 can include additional and/or alternative functional units than those described in the example of FIG. 1A.

The reagent adding section 128 includes a plurality of reagent input channels and corresponding valve assemblies configured to communicate with the control system such that one or more reagents can be selectively added to a selected droplet when the droplet is in the second segment of the microfluidic channel within the reagent adding section at a selected time. The example of FIG. 1A shows four reagent channels and corresponding valve assemblies. However, the broad concepts of the invention are not limited to a particular number of reagent channels. Alternatively, one, two or three could be used, or more than four could be used. In some cases, many more than four can be used. For example, tens or even hundreds could be included.

The reagent adding section 128 includes a portion of the microfluidic channel 120 in which a cross-section area is decreased relative to adjacent sections to stretch droplets across at least some of the plurality of reagent input channels, Some examples of a droplet stretching segment of the channel are described in more detail below. The reagent adding section 128 further includes a stabilizing-fluid input channel 132 and a corresponding valve assembly configured to communicate with the control system 114 such that a stabilizing fluid containing a surfactant can be selectively added to droplets within the droplet treatment system. The stabilizing fluid can be a carrier fluid such as that used to separate the plugs and droplets with the addition of a surfactant, for example. The stabilizing-fluid input channel 132 is arranged downstream from the plurality of reagent input channels 128 such that droplets can be stabilized after addition of reagent. In many applications, one of the plurality of reagents will be added. However, the broad concepts of the current invention are not limited to that example. Any combination of two or more of the available reagents could be added, if desired for a particular application.

In some embodiments, the reaction section or incubation section 130 includes a temperature control component. For example, the shaded area could be a Peltier component to heat and/or cool the reaction or incubation section. Other temperature control components could also be used, such as, but not limited to, resistive heating elements and/or heat conduction components that are in thermal contact with external heat sources or heat sinks. The temperature control component can also be adapted to communicate with the control system. This can permit maintaining a constant temperature and/or providing a programed temperature profile, either spatially along the microfluidic channel 120 and/or changing with time. Furthermore the microfluidic channel can have a serpentine path in the reaction section or incubation section 130 to allow for a compact arrangement with an extended path length. In some embodiments, as in some examples described in more detail below, the reaction section or incubation section 130 is an incubation section. As is illustrated in more detail below, the incubation section can be a plurality of subsections, such as, but not limited to three in the example, with corresponding separately controllable heating elements.

In some embodiments, the input system 102 includes a capillary tube 104 that is suitable to be loaded with the sequential stream of sample plugs with separation fluid between adjacent sample plugs. For example, a silica capillary tube could be used in some embodiments. However, the broad concepts of the current invention are not limited to this example. For example, without limitation, other cartridge or tube structures could be used.

As will be described in more detail below in reference to particular examples, capillary tube 104 of the input system 102 has a cross-sectional opening that extends beyond a cross-sectional opening of the input end 122 of the microfluidic channel 120. The input system 102 can further include an adapter that has a first end that substantially matches the cross-sectional opening of the capillary tube 104 and a second end that substantially matches the cross-sectional opening of the input end 122 of the microfluidic channel 120. In some embodiments, the adapter has a substantially smooth inner surface that tapers from the first end to the second end. In alternative embodiments, the adapter has a segmented inner surface that provides a plurality of steps to transition from the first end to the second end.

In some embodiments, the input system 102 can further include an automated sample loader 134 configured to load the capillary tube 104 with the sequential stream of sample plugs and with carrier fluid between adjacent sample plugs from a multi well plate and to deliver and fluidly connect the capillary tube and the adapter to the input end 122 of the microfluidic channel 120. In some embodiments, the automated sample loader 134 can have a linear three-axis stage to move the multi well plate while maintaining the capillary tube 104 fixed. Moving the multi well plate instead of the capillary tube 104 can be advantageous in some applications to prevent disturbing sample as it is being loaded. However, the capillary tube 104 could be moved instead of, or in addition to, the multi well plate in some embodiments.

The detection system 112 can be, or can include, an optical system. However, other embodiments can include additional or alternatives to optical systems. The optical system can be, but is not limited to, a multi-color confocal fluorescence spectroscopic (CFS) instrument.

Other detection systems are described in U.S. Pat. No. 8,248,609, granted on Aug. 21, 2012, the entire contents of which are hereby incorporated by reference.

The control system 114 can be configured to selectively, start, stop and regulate a flow speed of the output stream of droplets and the stream of treated droplets, for example.

The following examples describe some embodiments and some applications in more detail. However, the broad concepts of the current invention are not limited to the particular examples.

EXAMPLES

Maintaining global crop production has become increasingly important amidst a growing global population, and together with water scarcity, pollution, decreasing arable land, emergence of new pests, and possible climate change pose significant challenges. Toward this end, genetic marker assisted selection (MAS), wherein the plant breeding process relies on known DNA/RNA variations associated with traits of interest (e.g., productivity and disease resistance), has enormous potential to improve the efficiency and precision of conventional plant breeding. Performing MAS at the scale required for agricultural applications, however, requires screening a large number of plant samples against a large number of markers, thus presenting a critical need for novel tools that can meet this demand.

Figure 1B:
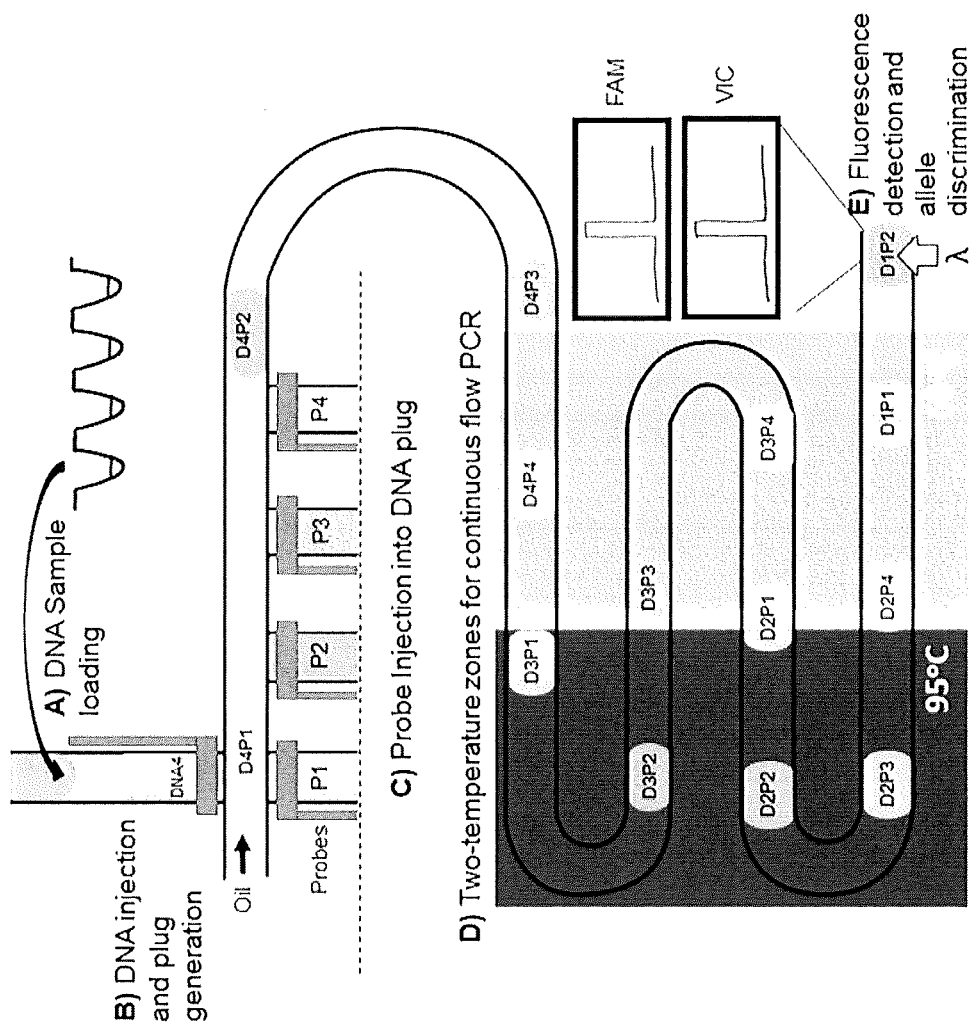
FIG. 1B is a schematic overview of a microfluidic droplet platform toward performing multiplexed, continuous flow, Taqman PCR-based genotyping for high-throughput MAS according to an embodiment of the current invention.
Figure 2:
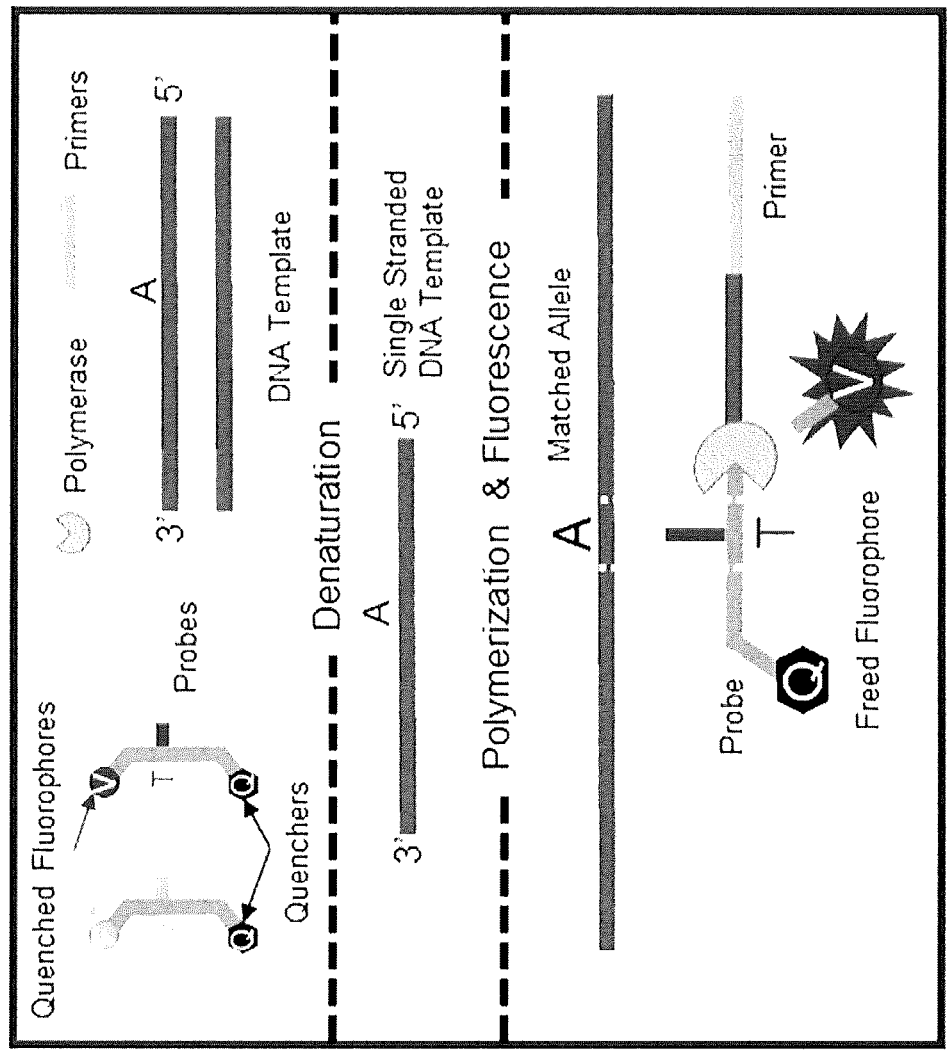
FIG. 2 is a schematic illustration showing allelic discrimination via TaqMan Polymerase Chain Reaction (PCR) assay.

Here we present a microfluidic droplet platform aimed towards performing multiplexed, continuous-flow, Taqman PCR-based genotyping for high-throughput MAS (FIG. 1B). The platform is designed to: 1) accept a large number of genomic DNA samples, 2) encapsulate samples into nL-sized droplets, 3) inject PCR reagents containing Taqman probes into sample droplets, 4) transport droplets through serpentine channels affixed at different temperatures to perform continuous-flow PCR, and 5) detect fluorescence in droplets to classify genotypes. The PCR assay employed in this work uses a FAM-fluorescent-dye-labeled Taqman probe and a VIC-fluorescent-dye-labeled Taqman probe so that each specific mutation in the genomic DNA can be classified as the FAM allele, the VIC allele, or heterozygous (both FAM and VIC alleles) (FIG. 2).

Figure 3:
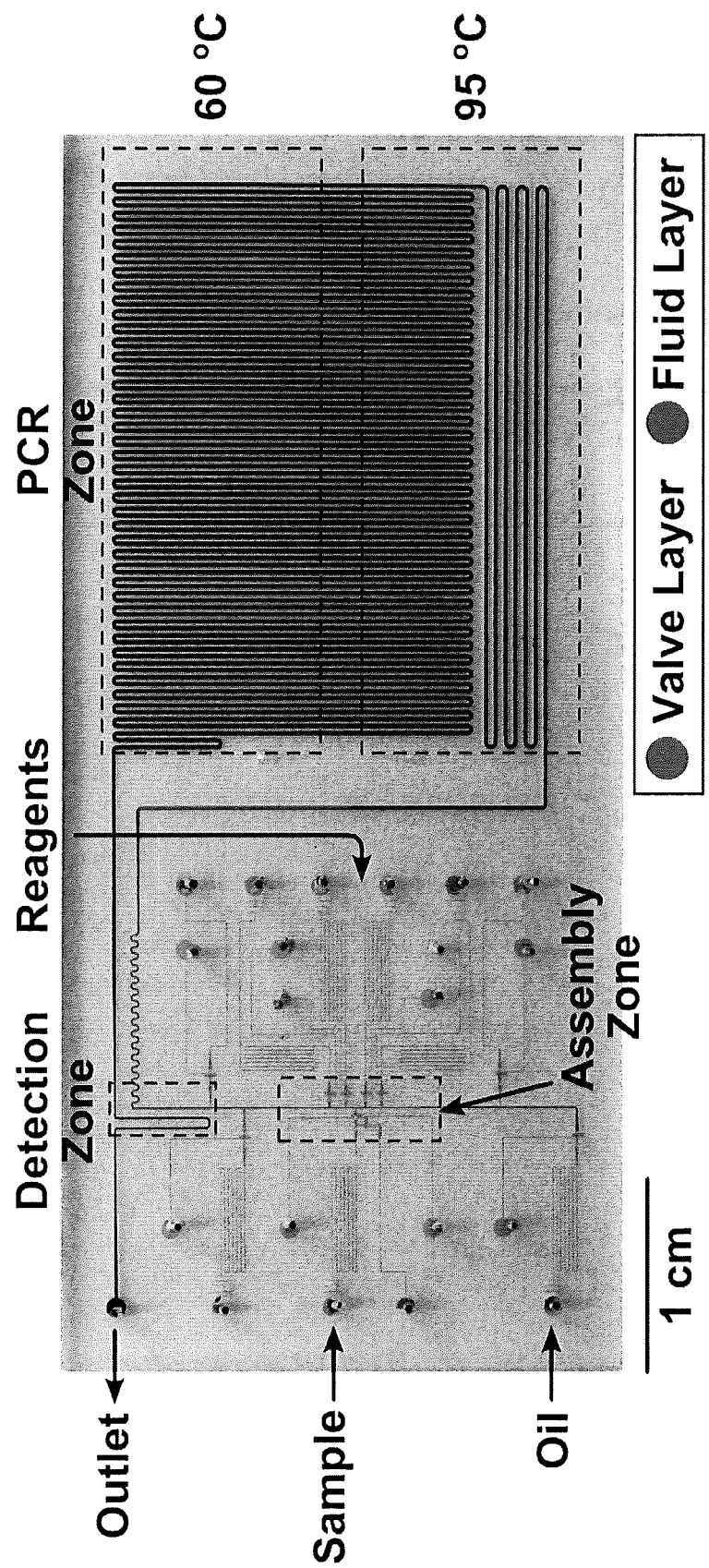
FIG. 3 is a schematic of a microfluidic chip according to an embodiment of the current invention.
Figure 4:
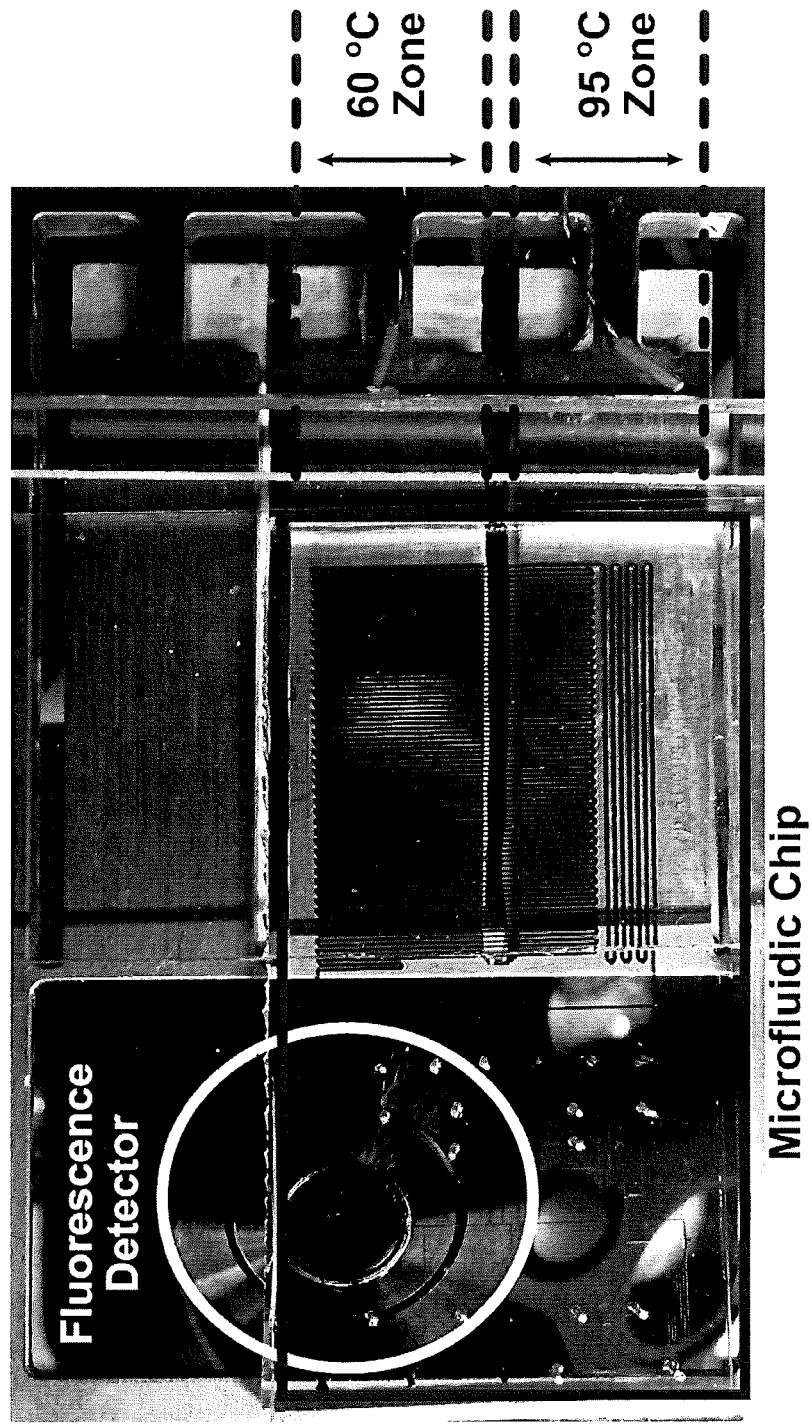
FIG. 4 shows an example of a chip according to an embodiment of the current invention during experimentation mounted on a custom plate with independent temperature zones (heated by peltier heaters) and an optical detection window.

The microfluidic chip is designed to support multiplexed droplet assembly and continuous-flow PCR; it entails a channel layer and a valve control layer and is fabricated via previously reported multilayer PDMS soft lithography technique (FIG. 3). The microfluidic valves are programmed to open and close on-demand for assembling sample and reagent droplets. Assembled droplets are subsequently pushed by carrier oil downstream before the next droplet is assembled. The droplets are pushed through the incubation channel while maintaining their sequence, providing a ready means for spatially indexing these droplets in high-throughput applications. The device is placed on a custom-fabricated plate with three independent temperature zones and an optical detection window (FIG. 4). Three temperature-controlled peltier heaters are thermally glued to the three temperature zones of the plate to deliver the required temperatures for PCR. The detection window allows fluorescence detection of each droplet in a sequential manner via a custom-built, multi-color confocal fluorescence spectroscopic (CFS) instrument.

Figure 5:
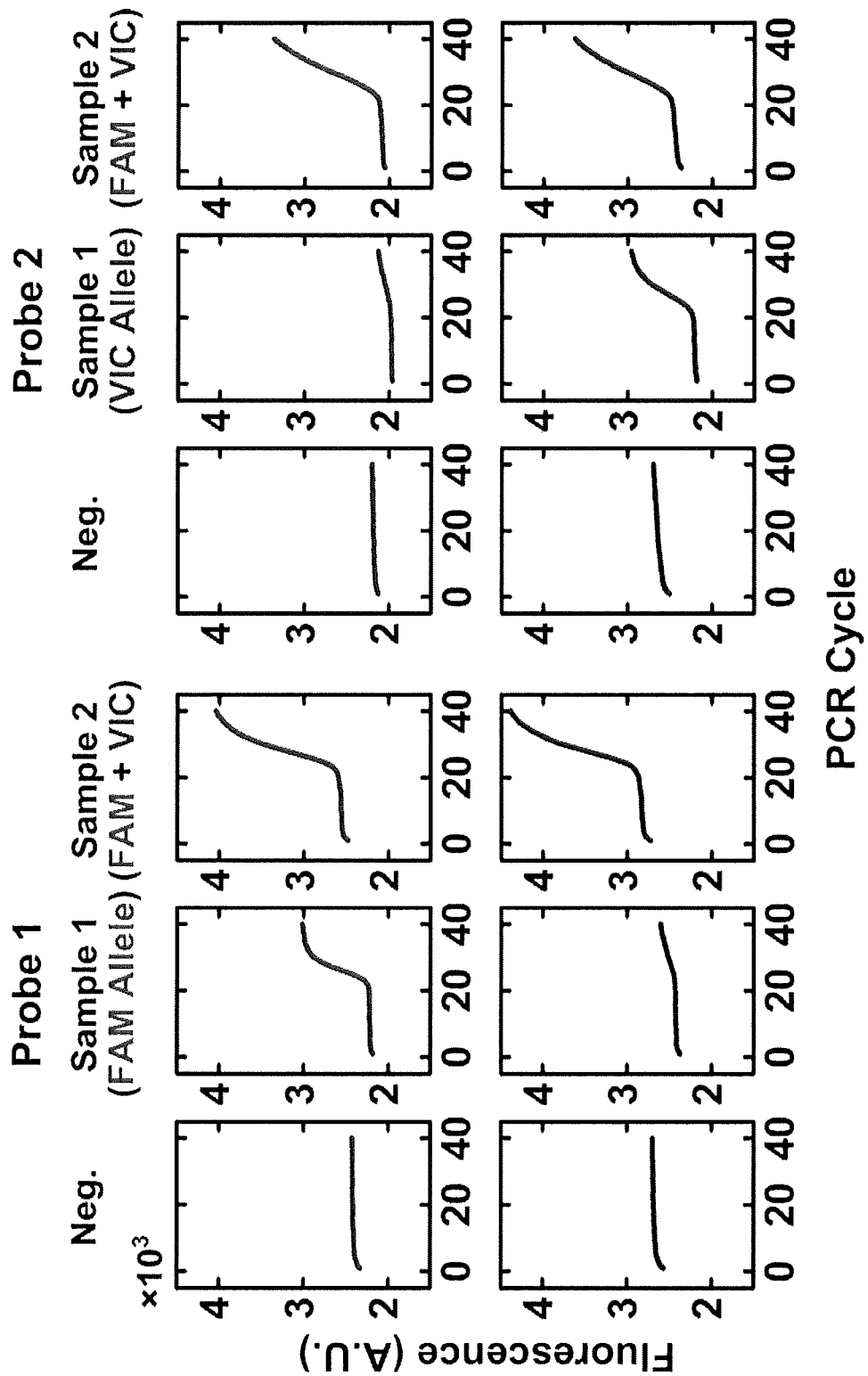
FIG. 5 shows graphs showing benchtop verification of Taqman PCR and allele classification.
Figure 6:
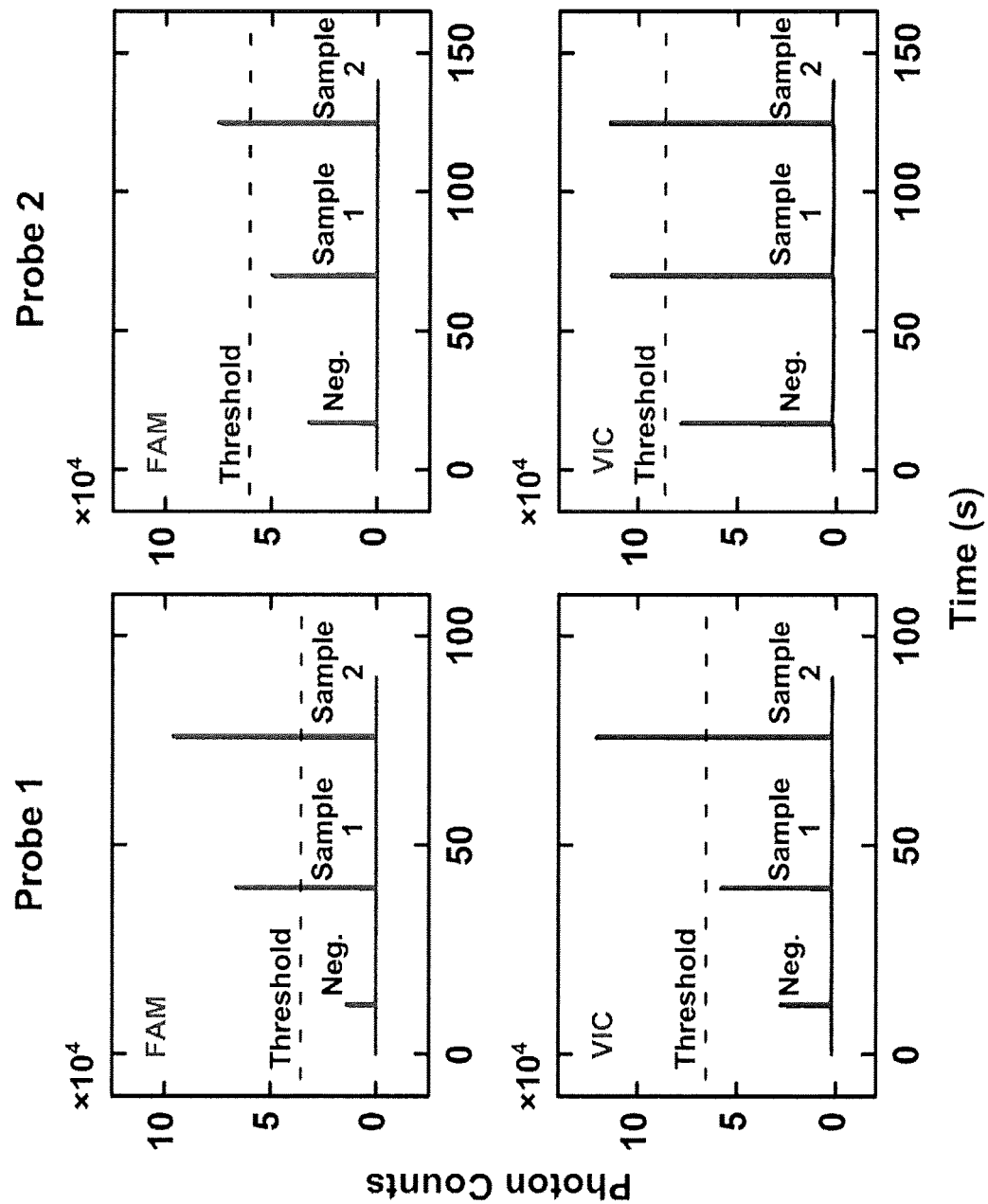
FIG. 6 shows graphs showing benchtop verification of Taqman PCR and allele classification.

The robustness of the Taqman PCR assay was first verified in the traditional tube and benchtop format. Here, we used two DNA samples and two sets of Taqman probes and correctly classified the alleles for these combinations (FIG. 5). These benchtop amplified products were then loaded into the chip, discretized into droplets, flown through the incubation channel, and detected by the CFS instrument. Specifically, the incubation zones on the chip were heated to the appropriate temperatures for PCR. The fluorescence peaks associated with droplets containing these benchtop amplified products (FIG. 6) indicated successful detection, which also suggested that evaporation of droplets and leaking of fluorophores were both tolerable in our chips.

REFERENCES

1 S. Y. Teh, R. Lin, L. H. Hung and A. P. Lee, *Lab. Chip*, 2008, 8, 198-220 (DOI:10.1039/b715524g).
2 A. Huebner, S. Sharma, M. Srisa-Art, F. Hollfelder, J. B. Edel and A. J. Demello, *Lab. Chip*, 2008, 8, 1244-1254 (DOI:10.1039/b806405a).
3 R. R. Pompano, W. Liu, W. Du and R. F. Ismagilov, *Annu, Rev, Anal. Chem.* (Palo Alto Calif.), 2011, 4, 59-81 (DOI:10.1146/annurev.anchem.012809.102303).
4 M. T. Guo, A. Rotem, J. A. Heyman and D. A. Weitz, *Lab. Chip*, 2012, (DOI: 10.1039/c21c21147e).
5 H. Song, D. L. Chen and R. F. Ismagilov, *Angew, Chem. Int. Ed Engl.*, 2006, 45, 7336-7356 (DOI:10.1002/anie.200601554).
6 P. Kumaresan, C. J. Yang, S. A. Cronier, R. G. Blazej and R. A. Mathies, *Anal. Chem.*, 2008, 80, 3522-3529 (DOI:10.1021/ac800327d).
7 N. R. Beer, B. J. Hindson, E. K. Wheeler, S. B. Hall, K. A. Rose, I. M. Kennedy and B. W. Colston, *Anal. Chem.*, 2007, 79, 8471-8475 (DOI:10.1021/ac701809w).
8 M. M. Kiss, L. Ortoleva-Donnelly, N. R. Beer, J. Warner, C. G. Bailey, B. W. Colston, J. M. Rothberg, D. R. Link and J. H. Leamon, *Anal. Chem.*, 2008, 80, 8975-8981.
9 A. Huebner, M. Srisa-Art, D. Holt, C. Abell, F. Hollfelder, A. J. deMello and J. B. Edel, *Chem. Commun*, (*Camb*), 2007, (12), 1218-1220 (DOI:10.1039/b618570c).
10 J. Clausell-Tormos, D. Lieber, J. C. Baret, A. El-Harrak, O. J. Miller, L. Frenz, J. Blouwolff, K. J. Humphry, S. Koster, H. Duan, C. Holtze, D. A. Weitz, A. D. Griffiths and C. A. Merten, *Chem. Biol.*, 2008, 15, 427-437 (DOI: 10.1016/j.chembiol.2008.04.004).
11 J. C. Baret, O. J. Miller, V. Taly, M. Ryckelynck, A. El-Harrak, L. Frenz, C. Rick, M. L. Samuels, J. B. Hutchison, J. J. Agresti, D. R. Link, D. A. Weitz and A. D. Griffiths, *Lab. Chip*, 2009, 9, 1850-1858 (DOI: 10.1039/b902504a).
12 W. Shi, J. Qin, N. Ye and B. Lin, *Lab. Chip*, 2008, 8, 1432-1435 (DOI:10.1039/b808753a).
13 W. Shi, H. Wen, Y. Lu, Y. Shi, B. Lin and J. Qin, *Lab. Chip*, 2010, 10, 2855-2863 (DOI:10.1039/c01c00256a).
14 B. Sobrino, M. Brion and A. Carracedo, *Forensic Sci. Int*, 2005, 154, 181-194 (DOI:10.1016/j.forsciint.2004.10.020).
15 P. K. Gupta, S. Rustgi and R. R. Mir, *Heredity* (*Edinb*), 2008, 101, 5-18 (DOI:10.1038/hdy.2008.35).
16 J. Ragoussis, *Annu. Rev. Genomics Hum. Genet.*, 2009, 10, 117-133 (DOI:10.1146/annurev-genom-082908-150116).
17 B. Veldhuisen, C. E. van der Schoot and M. de Haas, *Vox Sang.*, 2009, 97, 198-206 (DOI:10.1111/j.1423-0410.2009.01209.x).
18 R. Tewhey, J. B. Warner, M. Nakano, B. Libby, M. Medkova, P. H. David, S. K. Kotsopoulos, M. L. Samuels, J. B. Hutchison, J. W. Larson, E. J. Topol, M. P. Weiner, O. Harismendy, J. Olson, D. R. Link and K. A. Frazer, *Nat. Biotechnol.*, 2009, 27, 1025-1031 (DOI: 10.1038/nbt.1583).
19 E. Brouzes, M. Medkova, N. Savenelli, D. Marran, M. Twardowski, J. B. Hutchison, J. M. Rothberg, D. R. Link, N. Perrimon and M. L. Samuels, Proc, Natl. Acad. Sci. U, S. A., 2009, 106, 14195-14200 (DOI: 10.1073/pnas.0903542106).
20 A. B. Theberge, E. Mayot, A. El Harrak, F. Kleinschmidt, W. T. Huck and A. D. Griffiths, *Lab. Chip*, 2012, 12, 1320-1326 (DOI:10.1039/c21c21019c).
21 A. R. Abate, T. Hung, P. Mary, J. J. Agresti and D. A. Weitz, *Proc. Natl. Acad. Sci. U.S.A.*, 2010, 107, 19163-19166 (DOI:10.1073/pnas.1006888107).
22 L. Li, D. Mustafi, Q. Fu, V. Tereshko, D. L. Chen, J, D. Tice and R. F. Ismagilov, *Proc. Natl. Acad. Sci. U.S.A.* 2006, 103, 19243-19248 (DOI:10.1073/pnas.0607502103).
23 J. Q. Boedicker, L. Li, T. R. Kline and R. F. Ismagilov, *Lab. Chip*, 2008, 8, 1265-1272 (DOI:10.1039/b804911d).
24 S. Zeng, B. Li, X. Su, J. Qin and B. Lin, *Lab. Chip*, 2009, 9, 1340-1343 (DOI:10.1039/b821803j).

25 F. Guo, K. Liu, X. Ji, H. Ding, M. Zhang, Q. Zeng, W. Liu, S. Guo and X, Zhao, *Appl. Phys. Lett.,* 2010, 97, 233701-3.

26 H. Wang, K. Liu, K. J. Chen, Y. Lu, S. Wang, W. Y. Lin, F. Guo, K. Kamei, Y. C. Chen, M. Ohashi, M. Wang, M. A. Garcia, X. Z. Zhao, C. K. Shen and H. R. Tseng, *ACS Nano,* 2010, 4, 6235-6243 (DOI:10.1021/nn101908e).

27 M. A. Unger, H. P. Chou, T, Thorsen, A. Scherer and S. R. Quake, *Science,* 2000, 288, 113-116.

28 C. M. Puleo and T. H. Wang, *Lab. Chip,* 2009, 9, 1065-1072 (DOI:10.1039/b819605b).

29 C. M. Puleo, H. C. Yeh, K. J. Liu and T. H, Wang, *Lab. Chip,* 2008, 8, 822-825 (DOI:10.1039/b717941c).

30 T. D. Rane, C. M. Puleo, K. J. Liu, Y. Zhang, A. P. Lee and T. H. Wang, *Lab. Chip,* 2010, 10, 161-164 (DOI: 10.1039/b917503b).

31 J. Melin and S. R. Quake, *Annu. Rev. Biophys. Biomol. Struct.,* 2007, 36, 213-231 (DOI: 10.1146/annurev.biophys.36.040306.132646).

32 M. D. Abramoff, P. J. Magalhaes and S. J. Ram, *Biophotonics International,* 2004, 11, 36-42.

FURTHER REFERENCES

1. "Microfluidic cell culture systems for cellular analysis," J. H. Yeon and J.-K. Park, BioChip Journal, 1, 17 (2007).
2. "Ultra-low voltage MEMS switch using a folded hinge structure," M.-W. Kim, Y.-H. Song, S.-D. Ko, S.-J. Ahn, and J.-B. Yoon, Micro and Nano Systems Letters, 2, 2 (2014).
3. "Droplet electroporation in microfluidics for efficient cell transformation with or without cell wall removal," B. Qu, Y.-J. Eu, W.-J. Jeong, and D.-P. Kim, Lab on a Chip, 12, 4483 (2012).

The embodiments illustrated and discussed in this specification are intended only to teach those skilled in the art how to make and use the invention. In describing embodiments of the invention, specific terminology is employed for the sake of clarity. However, the invention is not intended to be limited to the specific terminology so selected. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

We claim:

1. A continuous droplet flow microfluidic system, comprising:
   a microfluidic chip comprising an optical detection section;
   a stage assembly comprising a microfluidic chip holder configured to receive said microfluidic chip and a plurality of heating elements arranged to heat a plurality of separate sections of said microfluidic chip to a corresponding plurality of different temperatures; and
   an optical detection system arranged to detect fluorescent light emitted from said optical detection section of said microfluidic chip,
   wherein said microfluidic chip comprises:
      a substrate;
      a channel control layer attached to said substrate; and
      a fluid flow layer attached to said channel control layer on an opposite side of said control layer from said substrate such that said fluid flow layer and said channel control layer define fluid channels within said fluid flow layer, said channel control layer and said fluid flow layer being formed from materials that do not require surface treatment for fluid flow through said fluid channels,
   wherein said channel control layer and said fluid flow layer define a main channel extending from a droplet generating section, extending through a reagent injection section, passing through a plurality of incubation sections, each incubation section having a separately selectable temperature, and passing through said optical detection section,
   wherein said main channel increases in width and height between said reagent injection section and said plurality of incubation sections, and
   wherein said optical detection section of said main channel has at least one of a decreased width or decreased height relative to said plurality of incubation sections to stretch droplets for detection.

2. The continuous droplet flow microfluidic system according to claim 1, wherein said droplet generating section is configured to receive a capillary comprising a plurality of sample plugs separated by an immiscible carrier fluid and to generate a plurality of droplets from each of said plurality of sample plugs.

3. The continuous droplet flow microfluidic system according to claim 2, wherein said plurality of droplets are between 0.1 nL and 200 nL.

4. The continuous droplet flow microfluidic system according to claim 2, wherein said plurality of droplets are between 0.5 nL and 100 nL.

5. The continuous droplet flow microfluidic system according to claim 1, wherein said droplet generating section is configured to receive a droplet generator.

6. The continuous droplet flow microfluidic system according to claim 5, further comprising an input system in fluid communication with said droplet generator,
   wherein said input system is configured to provide a sequential stream of sample plugs, and
   wherein said droplet generator is configured to receive the sequential stream of sample plugs.

7. The continuous droplet flow microfluidic system according to claim 5, further comprising a droplet treatment system arranged in fluid connection with said droplet generator.

8. The continuous droplet flow microfluidic system according to claim 5, wherein said droplet generator is configured to provide a stream of treated droplets in a sequential order.

9. The continuous droplet flow microfluidic system according to claim 5, wherein said droplet generator further comprises a valve assembly.

10. The continuous droplet flow microfluidic system according to claim 1, wherein said reagent injection section is configured to allow selected injection of at least one of a plurality of reagents into selected droplets as the droplets pass through said reagent injection section.

11. The continuous droplet flow microfluidic system according to claim 1, wherein said main channel has a serpentine path in each incubation section of said plurality of incubation sections.

12. The continuous droplet flow microfluidic system according to claim 1, wherein said optical detection system is a multi-color confocal fluorescence spectroscopic system.

13. A microfluidic chip, comprising;
   a substrate;
   a channel control layer attached to said substrate; and a fluid flow layer attached to said channel control layer on an opposite side of said control layer from said substrate such that said fluid flow layer and said channel control layer define fluid channels within said fluid flow layer, said channel control layer and said fluid flow layer being formed from materials that do not require surface treatment for fluid flow through said fluid channels, wherein said channel control layer and said fluid flow layer define a main channel extending from a droplet generating section, extending through a reagent injection section, passing through a plurality of incubation sections, each incubation section having a separately selectable temperature, and passing through an optical detection section, wherein said main channel increases in width and height between said reagent injection section and said plurality of incubation sections, and wherein said optical detection section of said main channel has at least one of a decreased width or decreased height relative to said plurality of incubation sections to stretch droplets for detection.

14. The microfluidic chip according to claim 13, wherein said droplet generating section is configured to receive a capillary comprising a plurality of sample plugs separated by an immiscible carrier fluid and to generate a plurality of droplets from each of said plurality of sample plugs.

15. The microfluidic chip according to claim 14, wherein said plurality of droplets are between 0.1 nL and 200 nL.

16. The microfluidic chip according to claim 14, wherein said plurality of droplets are between 0.5 nL and 100 nL.

17. The microfluidic chip according to claim 14, wherein said reagent injection section is configured to allow selected injection of at least one of a plurality of reagents into selected droplets as the droplets pass through said reagent injection section.

18. The microfluidic chip according to claim 14, wherein said main channel has a serpentine path in each incubation section of said plurality of incubation sections.

* * * * *